United States Patent [19]

Marinak et al.

[11] Patent Number: 4,497,955
[45] Date of Patent: Feb. 5, 1985

[54] PREPARATION OF 2-CHLORO-5-TRICHLOROMETHYL PYRIDINE FROM LOWER CHLORINATED BETA-PICOLINES

[75] Inventors: Michael J. Marinak, Kelso; John L. Simonson, Longview, both of Wash.

[73] Assignee: Kalama Chemical, Inc., Kalama, Wash.

[21] Appl. No.: 422,755

[22] Filed: Sep. 24, 1982

[51] Int. Cl.$^3$ .............................. C07D 213/61
[52] U.S. Cl. ................................... 546/345
[58] Field of Search ........................ 546/345

[56]  References Cited

U.S. PATENT DOCUMENTS

| | | | |
|---|---|---|---|
| 3,173,919 | 3/1965 | Johnston et al. | 546/345 |
| 3,224,950 | 12/1965 | Johnston et al. | 546/345 |
| 3,418,323 | 12/1968 | Johnston et al. | 546/345 |
| 3,420,833 | 1/1969 | Taplin | 546/345 |
| 3,424,754 | 1/1969 | Taplin | 546/345 |
| 4,205,175 | 5/1980 | Bowden et al. | 546/345 |
| 4,241,213 | 12/1980 | Nishiyama et al. | 546/345 |

FOREIGN PATENT DOCUMENTS

| | | | |
|---|---|---|---|
| 55-76860 | 6/1980 | Japan | 546/345 |
| 957276 | 5/1964 | United Kingdom | 546/345 |

OTHER PUBLICATIONS

Groggins, *Unit Processes in Organic Synthesis* (5th Edition 1958), pp. 19, 32, 43, 73, 77, 237, 408, 410, 506, 509, 510, 517, 518, 520, 521, 535 and 536).
Kirk–Othmer, *Encyclopedia of Chemical Technology*, vol. 3, (3rd Edition), pp. 780 and 781.
McBee et al., *Industrial and Engineering Chemistry*, vol. 39, pp. 389–391, (1947).
Chemical Abstracts, 88: 200981z (1978).
Chemical Abstracts, 90: 120672a (1979).

*Primary Examiner*—Henry R. Jiles
*Assistant Examiner*—Robert C. Whittenbaugh
*Attorney, Agent, or Firm*—Graybeal & Cullom

[57] ABSTRACT

A non-catalytic liquid phase chlorination of lower chlorinated beta-picolines comprising 3-trichloromethyl pyridine, 2-chloro-5-dichloromethyl pyridine, or mixtures thereof, to improve the yield of 2-chloro-5-trichloromethyl pyridine, an intermediate useful in the preparation of medicines and agricultural chemicals, especially herbicides.

10 Claims, No Drawings

PREPARATION OF 2-CHLORO-5-TRICHLOROMETHYL PYRIDINE FROM LOWER CHLORINATED BETA-PICOLINES

BACKGROUND OF THE INVENTION

1. Field of the Invention

Non-catalytic liquid phase chlorination of lower chlorinated beta-picolines to improve the yield of 2-chloro-5-trichloromethyl pyridine.

2. Description of the Prior Art

Bowden et al U.S. Pat. No. 4,205,175 and Nishiyama et al U.S. Pat. No. 4,241,213 teach vapor phase chlorination processes by means of which beta-picoline is chlorinated to produce 2-chloro-5-trichloromethyl pyridine, which compound is useful in the preparation of medicines and agricultural chemicals, especially herbicides. No prior process is known to applicants for producing 2-chloro-5-trichloromethyl pyridine by liquid phase chlorination.

SUMMARY OF THE INVENTION

It has now been discovered that partially chlorinated beta-picolines, such as the reaction products obtained by vapor phase chlorination according to the processes disclosed in the foresaid U.S. Pat. Nos. 4,205,175 and 4,241,213, containing substantial proportions of 3-trichloromethyl pyridine and 2-chloro-5-dichloromethyl pyridine, can be further chlorinated in the liquid phase to substantially improve the yield of 2-chloro-5-trichloromethyl pyridine. Reaction temperature and time of reaction significantly affect the yield of 2-chloro-5-trichloromethyl pyridine, it having been further found that the reaction temperature should be at least about 130° C. and not more than about 160° C. since lesser temperatures result in no substantial further chlorination and greater temperatures result in increased ring chlorination and consequent loss of the desired product. Residence time is readily controllable to maximize yield and a reaction time of about 8 hours at a temperature of 140° C. is typical for optimum yield of 2-chloro-5-trichloromethyl pyridine.

DESCRIPTION OF THE PREFERRED EMBODIMENTS

In carrying out the present invention, gaseous chlorine is sparged into a batch reactor containing an initial charge of a partially chlorinated beta-picoline mixture comprising substantial amounts of 3-trichloromethyl pyridine and 2-chloro-5-dichloromethyl pyridine, at a rate to ensure excess chlorine in the reactor vent, the reactor being heated to a temperature in the range from about 130° C. to about 160° C., at which temperature the reaction mixture is in liquid phase.

EXAMPLE 1

To obtain a mixture of partially chlorinated beta-picolines for use as the initial charge for the reaction of the present invention, a vapor phase chlorination of beta-picoline was carried out under conditions as disclosed in Example 1 of Nishiyama et al U.S. Pat. No. 4,241,213, and utilizing a reactor temperature of 390° C. (rather than 400° C. in the patent Example). About 61 grams/hour of chlorine were mixed with 150 grams/hour of carbon tetrachloride and the resulting mixture was vaporized, superheated, and transferred into a cylindrical reactor 5 centimeters in diameter and 30 centimeters long. In this reactor the premixed chlorine and carbon tetrachloride were rapidly mixed with about 19 grams/hour of superheated beta-picoline vapors. The residence time in the reactor was about 10 seconds.

Analysis of the quenched material is listed below in Table ONE.

TABLE ONE

| Constituent Compound | Initial Analysis | Chlorination Times and Temperatures | |
|---|---|---|---|
| | | After 8 hrs 140° C. | After 8 hrs at 140° C. + 6 hrs at 165° C. |
| 3-CCl$_3$ pyridine | 11.6% | 3.4% | 1.4% |
| 2-Cl-5-CHCl$_2$ pyridine | 3.6 | 0.9 | — |
| 2-Cl-5-CCl$_3$ pyridine | 62.4 | 77.2 | 76.7 |

EXAMPLE 2

To carry out the process of the present invention, the quenched material from Example 1 was placed in a batch reactor and 70 grams/hour chlorine sparged into the mixture which was heated to 140° C. Initially the viscosity of the mixture had the consistency of honey at both room temperature and 140° C. After eight hours of chlorination the mixture was fluid and crystalline upon cooling to room temperature. The concentration of the lower chlorinated beta-picolines such as 3-trichloromethyl pyridine and 2-chloro-5-dichloromethyl pyridine had decreased from 11.6 percent and 3.6 percent to 3.4 percent and 0.9 percent respectively. In addition the concentration of 2-chloro-5-trichloromethyl pyridine had increased from 62.4 percent to 77.2 percent. An additional 6 hours of chlorination at 165° C. resulted in a slight decrease of 2-chloro-5-trichloromethyl pyridine to 76.7 percent, a complete disappearance of the 2-chloro-5-dichloromethyl pyridine and a reduction of the concentration of 3-trichloromethyl pyridine to 1.4 percent. These data are also tabulated in Table ONE, above. As will be noted, the concentration of 2-chloro-5-trichloromethyl pyridine was increased from 62.4% to 76.7%, amounting to a greater than 20 percent yield increase, as compared with the product directly out of the vapor phase reactor. The resultant chlorinated mixture was a fluid, tractable liquid at the reaction temperature, but tended to crystallize at room temperature.

It is characteristic of the process of the invention that the optimum reaction temperature is dependent on the initial reactant concentration and the residence time during chlorination. A batch chlorination is considered the most effective method of accomplishing the reaction because it allows for the maximum increase in concentration of the desired 2-chloro-5-trichloromethyl pyridine in the reaction product, which may then be purified by any of several known techniques such as vacuum distillation, crystallization, or solvent extraction. The chlorine fed to the reaction is preferably sparged into the reaction mass near the bottom thereof and the resulting agitation is sufficient to complete the reaction. The hydrogen chloride and chlorine vented as outgas from the reaction can be collected, purified and the chlorine recycled in a manner conventional to this type of liquid phase reaction.

The foregoing Example 2 is simply illustrative of liquid phase methods characteristic of the invention and is not to be construed as limiting the invention. Observation of reaction conditions and results indicate the process is operable in the temperature range of about 130° C. to about 160° C., the lower limit being dictated by there being essentially no reaction at temperatures lower than about 130° C. and the upper limit being dictated by the fact that there is lesser yield of the desired product at temperatures in excess of about 160° C.

What is claimed is:

1. The process of producing 2-chloro-5-trichloromethyl pyridine from mixtures containing lower chlorinated beta-picolines selected from the group consisting of 3-trichloromethyl pyridine, 2-chloro-5-dichloromethyl pyridine, and mixtures thereof, said process comprising non-catalytic liquid phase chlorination of such lower chlorinated beta-picolines at a temperature of from about 130° C. to about 160° C. for a time to substantially maximize the 2-chloro-5-trichloromethyl pyridine content of the chlorinated product.

2. The process of claim 1, wherein the temperature is maintained at about 140° C.

3. The process of claim 1 or 2, wherein the material is chlorinated for a period of about 8 hours.

4. The process of claim 1, wherein chlorination is continued until substantially all 2-chloro-5-dichloromethyl pyridine is converted to 2-chloro-5-trichloromethyl pyridine.

5. The process of claim 1, wherein the 2-chloro-5-trichloromethyl pyridine content of the material is increased at least about 20% by weight and the resultant chlorinated mixture is a fluid, tractable liquid at the reaction temperature.

6. The process of increasing the 2-chloro-5-trichloromethyl pyridine yield in a reactor charge of chlorinated beta-picolines comprising 2-chloro-5-trichloromethyl pyridine, 3-trichloromethyl pyridine and 2-chloro-5-dichloromethyl pyridine, said process comprising:
   (a) heating such reactor charge at a temperature of from about 130° C. to about 160° C. at substantially atmospheric pressure; and
   (b) while maintaining the charge in liquid phase within said temperature range, sparging chlorine into the material in the absence of a catalyst and at a rate to ensure excess chlorine in the reactor vent for a time to convert substantial quantities of the 3-trichloromethyl pyridine and 2-chloro-5-dichloromethyl pyridine to 2-chloro-5-trichloromethyl pyridine.

7. The process of claim 6, wherein the temperature is maintained at about 140° C.

8. The process of claim 6 or 7, wherein the material is chlorinated for a period of about 8 hours.

9. The process of claim 6, wherein chlorination is continued until substantially all 2-chloro-5-dichloromethyl pyridine is converted to 2-chloro-5-trichloromethyl pyridine.

10. The process of claim 6, wherein the 2-chloro-5-trichloromethyl pyridine content of the material is increased at least about 20% by weight and the resultant chlorinated mixture is a fluid, tractable liquid at the reaction temperature.

* * * * *